US008518699B2

(12) United States Patent
Buerstedde et al.

(10) Patent No.: US 8,518,699 B2
(45) Date of Patent: Aug. 27, 2013

(54) METHODS FOR GENETIC DIVERSIFICATION IN GENE CONVERSION ACTIVE CELLS

(75) Inventors: Jean-Marie Buerstedde, München (DE); Hiroshi Arakawa, München (DE)

(73) Assignee: GSF-Forschungszentrum fur Umwelt und Gesundheit, GmbH, Neuherberg (DE)

( * ) Notice: Subject to any disclaimer, the term of this patent is extended or adjusted under 35 U.S.C. 154(b) by 60 days.

(21) Appl. No.: 10/590,211

(22) PCT Filed: Feb. 23, 2005

(86) PCT No.: PCT/EP2005/001897
§ 371 (c)(1),
(2), (4) Date: Aug. 22, 2006

(87) PCT Pub. No.: WO2005/080552
PCT Pub. Date: Sep. 1, 2005

(65) Prior Publication Data
US 2007/0186292 A1 Aug. 9, 2007

(30) Foreign Application Priority Data

Feb. 23, 2004 (EP) .................................. 004004062

(51) Int. Cl.
*C12N 15/00* (2006.01)
*C12N 5/02* (2006.01)
*C12N 5/071* (2010.01)
*A61K 48/00* (2006.01)
*A01K 67/027* (2006.01)

(52) U.S. Cl.
USPC .......... 435/455; 435/325; 435/372.2; 800/14; 514/44

(58) Field of Classification Search
None
See application file for complete search history.

(56) References Cited

U.S. PATENT DOCUMENTS

2005/0026246 A1* 2/2005 Sale et al. ..................... 435/69.1
2006/0052585 A1* 3/2006 Grawunder et al. ....... 530/388.1

FOREIGN PATENT DOCUMENTS

WO  WO 00/22111 A1  4/2000
WO  WO 02/100998 A2  12/2002

OTHER PUBLICATIONS

Kim et al. Mol. Cell Biol. 10:3224-3231; 1990.*
Arakawa et al. PLoS Biol. 2:0967-0974; 2004.*
Arakawa et al., "Immunoglobulin Gene Conversion: Insights from Bursal B Cells and the DT40 Cell Line," *Developmental Dynamics*, 229:458-464 (2004).
Diaz et al., "Evolution of Somatic Hypermutation and Gene Conversion in Adaptive Immunity," *Immunological Reviews*, 162:13-24 (1998).
Sale et al., "TdT-Accessible Breaks are Scattered over the Immunoglobulin V Domain in a Constitutively Hypermutating B Cell Line," *Immunity*, 9:859-869 (1998).
Yélamos et al., "Targeting of non-lg Sequences in Place of the V Segment by Somatic Hypermutation," *Nature*, 376:225-229 (1995).
International Search Report from PCT/EP2005/001897 (mailed Aug. 17, 2005).
Arakawa et al., "Immunoglobulin gene hyperconversion ongoing in chicken splenic germinal centers", *The EMBO Journal* 15(10):2540-2546 (1996).
Arakawa et al., "Oligoclonal Development of B Cells Bearing Discrete Ig Chains in Chicken Single Germinal Centers", *The Journal of Immunology* 160:4232-4241 (1998).
Arakawa et al., "Mutant loxP vectors for selectable marker recycle and conditional knock-outs", *BMC Biotechnology* 1:7 (2001).
Arakawa et al., "Requirement of the Activation-Induced Deaminase (AID) Gene for Immunoglobulin Gene Conversion", *Science* 295:1301-1306 (2002).
Bachl et al., "An immunoglobulin mutator that targets G-C base pairs", *Proc. Natl. Acad. Sci. USA*, 93:851-855 (1996).
Barreto et al., "C-Terminal Deletion of AID Uncouples Class Switch Recombination from Somatic Hypermutation and Gene Conversion", *Molecular Cell* 12:501-508 (2003).
Bezzubova et al., "Reduced X-Ray Resistance and Homologous Recombination Frequencies in a RAD54$^{-/-}$ Mutant of the Chicken DT40 Cell Line", *Cell* 89:185-193 (1997).
Buerstedde et al., "Light chain gene conversion continues at high rate in an ALV-induced cell line", *The EMBO Journal* 9(3):921-927 (1990).
Buerstedde et al., "Increased Ratio of Targeted to Random Integration after Transfection of Chicken B Cell Lines", *Cell* 67:179-188 (1991).
Butler, "Immunoglobulin diversity, B-cell and antibody repertoire development in large farm animals", *Rev. sci. tech. Off. int. Epiz.* 17(1):43-70 (1998).
Carlson et al., "Templated insertions in the rearranged chicked $Ig_L$ V gene segment arise by intrachromosomal gene conversion", *Genes & Development* 4:536-547 (1990).
Di Noia et al., "Altering the pathway of immunoglobulin hypermutation by inhibiting uracil-DNA glycosylase", *Nature* 419:43-48 (2002).

(Continued)

*Primary Examiner* — Janet Epps-Smith
(74) *Attorney, Agent, or Firm* — Arnold & Porter LLP

(57) ABSTRACT

The invention relates to a modified lymphoid cell having gene conversion fully or partially replaced by hypermutation, wherein said cell has no deleterious mutations in genes encoding paralogues and analogues of the RAD51 protein, and wherein said cell is capable of directed and selective genetic diversification of a target nucleic acid by hypermutation or a combination of hypermutation and gene conversion. The invention also relates to a method for diversifying any transgenic target gene in said cell. Preferably, the target gene is integrated into the immunoglobulin light or heavy chain locus by targeted integration.

25 Claims, 6 Drawing Sheets

(56) References Cited

OTHER PUBLICATIONS

Drake et al., "Rates of Spontaneous Mutation", *Genetics* 148:1667-1686 (1998).

Faili et al., "AID-dependent somatic hypermutation occurs as a DNA single-strand event in the BL2 cell line", *Nature Immunology* 3(9):815-821 (2002).

Lebecque et al., "Boundaries of Somatic Mutation in Rearranged Immunoglobulin Genes: 5' Boundary is Near the Promoter, and 3' Boundary is ~1 kb from V(D)J Gene", *J. Exp. Med.* 172:1717-1727 (1990).

Lundberg et al., "High-fidelity amplification using a thermostable DNA polymerase isolated from *Pyrococcus furiosus*", *Gene* 108:1-6 (1991).

Martin et al., "Somatic hypermutation of the AID transgene in B and non-B cells", *PNAS* 99(19):12304-12308 (2002).

Milstein et al., "The maturation of the antibody response", *Immunoglobulin Genes*, 2nd Edition, pp. 57-81 (1995).

Muramatsu et al., "Specific Expression of Activation-induced Cytidine Deaminase (AID), a Novel Member of the RNA-editing Deaminase Family in Germinal Center B Cells", *The Journal of Biological Chemistry* 274(26):18470-18476(1999).

Muramatsu et al., "Class Switch Recombination and Hypermutation Require Activation-Induced Cytidine Deaminase (AID), a Potential RNA Editing Enzyme", *Cell* 102:553-563 (2000).

Revy et al., "Activation-Induced Cytidine Deaminase (AID) Deficiency Causes the Autosomal Recessive Form of the Hyper-IgM Syndrome (HIGM2)", *Cell* 102:565-575 (2000).

Reynaud et al., "A Hyperconversion Mechanism Generates the Chicken Light Chain Preimmune Repertoire", *Cell* 48:379-388 (1987).

Sale et al., "Ablation of XRCC2/3 transforms immunoglobulin V gene conversion into somatic hypermutation", *Nature* 412:921-926 (2001).

Ta et al., "AID mutant analyses indicate requirement for class-switch-specific cofactors", *Nature Immunology* 4(9):843-848 (2003).

Yoshikawa et al., "AID Enzyme-Induced Hypermutation in an Actively Transcribed Gene in Fibroblasts", *Science* 296:2033-2036 (2002).

Arakawa et al., "Protein evolution by hypermutation and selection in the B cell line DT40," *Nucleic Acids Research* 36(1) el pp. 1-11 (2008).

Blagodatski et al., "A *cis*-Acting Diversification Activator Both Necessary and Sufficient for AID-Mediated Hypermutation," *PLOS Genetics* 5(1) el 000332 (2009).

* cited by examiner

METHODS FOR GENETIC DIVERSIFICATION IN GENE CONVERSION ACTIVE CELLS

CROSS REFERENCE TO RELATED APPLICATIONS

The present application is a national phase application under 35 U.S.C. §371 of International Application No. PCT/EP2005/001897, filed Feb. 23, 2005, which claims the benefit of EP Application No. 04004062.8, filed Feb. 23, 2004.

The present invention relates to a method for directed and selective genetic diversification of a target nucleic acid sequence or gene product by exploiting the relationship between immunoglobulin gene conversion and hypermutation in antibody-producing cells, as well as to cells and cell lines capable of said genetic diversification.

Many approaches to the generation of diversity in gene products rely on the generation of a very large number of mutants which are then selected using powerful selection technologies. However, these systems have a number of disadvantages. If the mutagenesis is done in vitro on gene constructs which are subsequently expressed in vitro or as transgenes in cells or animals, the gene expression in the physiological context is difficult and the mutant repertoire is fixed in time. If mutagenesis is on the other hand performed in living cells, it is difficult to direct mutations to a target nucleic acid where they are desired. Therefore the efficiency of isolating molecules with improved activity by repeated cycles of mutations and selection with sufficient efficiency is limited. Moreover, random mutagenesis in vivo is toxic and likely to induce a high level of undesirable secondary mutations.

In nature, directed diversification of a selected nucleic acid sequence takes place in the rearranged V(D)J segments of the immunoglobulin (Ig) gene loci. The primary repertoire of antibody specificities is generated by a process of DNA rearrangement involving the joining of immunoglobulin V, D, and J gene segments. Following antigen encounter, the rearranged V(D)J segments in those B cells, whose surface Ig can bind the antigen with low or moderate affinity, are subjected to a second wave of diversification by hypermutation. This so-called somatic hypermutation generates the secondary repertoire from which increased binding specificities are selected thereby allowing affinity maturation of the humoral immune response (Milstein and Rada, 1995).

The mouse and man immunoglobulin loci contain large pools of V, D and J gene segments which can participate in the V(D)J rearrangement, so that significant diversity is created at this stage by random combination. Other species such as chicken, rabbit, cow, sheep and pig employ a different strategy to develop their primary Ig repertoire (Butler, 1998). After the rearrangement of a single functional V and J segment, further diversification of the chicken light chain gene occurs by gene conversion in a specialized lymphoid organ, the Bursa of Fabricius (Reynaud et al., 1987; Arakawa and Buerstedde, in press). During this process, stretches of sequences from non-functional pseudo-V-genes are transferred into the rearranged V-gene. The twenty-five pseudo-V-genes are situated upstream of the functional V-gene and share sequence homology with the V-gene. Similar to the situation in men and mice, affinity maturation after antigen encounter takes place by hypermutation in the splenic germinal centers of the chicken (Arakawa et al., 1996).

All three B cell specific activities of Ig repertoire formation—gene conversion (Arakawa et al., 2002), hypermutation and isotype switch recombination (Muramatsu et al., 2000; Revy et al., 2000)—require expression of the Activation Induced Deaminase (AID) gene. Whereas it was initially proposed that AID is a DNA editing enzyme (Muramatsu et al., 1999), more recent studies indicate that AID directly modifies DNA by deamination of cytosine to uracil (Di Noia and Neuberger, 2002). However, the cytosine deamination activity must be further regulated, because only differences in the type, the location and the processing of the AID-induced DNA modification can explain the selective occurrence of recombination or hypermutation in different species and B cell environments. Based on the finding that certain AID mutations affect switch recombination, but not somatic hypermutation, it was suggested that AID needs the binding of a co-factor to start switch recombination (Ta et al., 2003; Barreto et al., 2003).

Analysis of DT40 knock-out mutants indicates that the RAD54 gene (Bezzubova et al., 1997) and other members of the RAD52 recombination repair pathway are needed for efficient Ig gene conversion (Sale et al., 2001). Disruption of RAD51 analogues and paralogues reduces Ig gene conversion and induces hypermutation in the rearranged light chain gene (Sale et al., 2001) suggesting that a defect in DNA repair by homologous recombination can shift Ig gene conversion to hypermutation.

Recently, first cell systems have been developed which exploit the phenomenon of somatic hypermutation in the immunoglobulin locus to generate mutants of a target gene in constitutive and directed manner. These cell systems allow to prepare a gene product having a desired activity by cyclical steps of mutation generation and selection. Thus, WO 00/22111 and WO 02/100998 describe a human Burkitt lymphoma cell line (Ramos) which is capable of directed constitutive hypermutation of a specific nucleic acid region. This mutated region can be the endogenous rearranged V segment or an exogenous gene operatively linked to control sequences which direct hypermutation. A significant disadvantage of this cell system is that human cells cannot be efficiently genetically manipulated by targeted integration, since transfected constructs insert primarily at random chromosomal positions.

WO 02/100998 also describes another cell system for generating genetic diversity in the Ig locus which is based on the chicken B cell line DT40. DT40 continues gene conversion of the rearranged light chain immunoglobulin gene during cell culture (Buerstedde et al., 1990). Importantly, this cell line has a high ratio of targeted to random integration of transfected constructs thus allowing efficient genetic manipulation (Buerstedde and Takeda, 1991). According to WO 02/100998, deletion in DT40 of the paralogues of the RAD51 gene which are involved in homologous recombination and DNA repair led to a decrease in gene conversion and a simultaneous activation of hypermutation of the rearranged V segment. However, the main disadvantage of this system is that the mutant cells have a DNA repair deficiency as reflected by X-ray sensitivity and chromosomal instability. The mutants also have a low proliferation rate and a low gene targeting efficiency. Therefore this system is poorly suited for efficient gene diversification and selection.

The present invention overcomes the disadvantages of the prior art systems and provides further advantages as well.

SUMMARY OF THE INVENTION

In the first aspect of the invention there is provided a genetically modified lymphoid cell having gene conversion fully or partially replaced by hypermutation, wherein said cell has no deleterious mutations in genes encoding paralogues and analogues of the RAD51 gene which encode important homologous recombination factors. Specifically, the cell contains wild-type homologous recombination factors. Due to the intact homologous recombination machinery, the cell according to the invention is recombination and repair proficient and has a normal proliferation rate.

The cell of the invention is an immunoglobulin-expressing B lymphocyte derived from animal species which use the mechanism of gene conversion for developing their immunoglobulin repertoire. These species are for example chicken, sheep, cow, pig and rabbit. Preferably, the cell is derived from a chicken Bursal lymphoma. Most preferably, the cell is derived from or related to the DT40 cell line.

In a further embodiment, the cell according to the invention is capable of directed and selective genetic diversification of a target nucleic acid by hypermutation or a combination of hypermutation and gene conversion. The target nucleic acid may encode a protein or possess a regulatory activity. Examples of proteins are an immunoglobulin chain, a selection marker, a DNA-binding protein, an enzyme, a receptor protein or a part thereof. In a preferred embodiment, the target nucleic acid is the V(D)J segment of a rearranged human immunoglobulin gene. Examples of regulatory nucleic acids are a transcription regulatory element or a RNAi sequence.

In an embodiment, in which the target nucleic acid is diversified by a combination of hypermutation and gene conversion, the cell according to the invention contains at least one sequence capable of serving as a gene conversion donor for the target nucleic acid.

In a further embodiment, the target nucleic acid is an exogenous nucleic acid operably linked to control nucleic acid sequences that direct genetic diversification.

In an additional embodiment, the target nucleic acid is expressed in the cell according to the invention in a manner that facilitates selection of cells which exhibit a desired activity. The selection can be a direct selection for the activity of the target nucleic acid within the cell, on the cell surface or outside the cell. Alternatively, the selection can be an indirect selection for the activity of a reporter nucleic acid.

In a further embodiment, the invention provides for genetic means to modulate the genetic diversification of the target nucleic acid in the cell according to the invention. The modulation can be by modification of cis-acting regulatory sequences, by varying the number of gene conversion donors, or by modification of trans-acting regulatory factors such as activation-induced deaminase (AID) or a DNA repair or recombination factor other than a RAD51 analogue or paralogue. The cell preferably expresses activation-induced deaminase (AID) conditionally.

In a second aspect, there is provided a cell line derived from a cell according to the invention. In a preferred embodiment, the cell line is DT40 or a modification thereof.

In a third aspect, there is provided a transgenic non-human animal containing a lymphoid cell having gene conversion fully or partially replaced by hypermutation, wherein said cell has no deleterious mutations in genes encoding paralogues and analogues of the RAD51 protein, and wherein said cell is capable of directed and selective genetic diversification of a transgenic target nucleic acid by hypermutation or a combination of hypermutation and gene conversion. In a preferred embodiment, the animal is chicken.

In a further aspect, the invention provides a method for preparing a cell capable of directed and selective genetic diversification of a target nucleic acid by hypermutation or a combination of hypermutation and gene conversion. The method comprises (a) transfecting a lymphoid cell capable of gene conversion with a genetic construct containing the target nucleic acid, and (b) identifying a cell having the endogenous V-gene segment of a part thereof replaced with the target nucleic acid.

According to a further embodiment, the genetic construct containing the target nucleic acid further contains at least one nucleic acid capable of serving as a gene conversion donor for the target nucleic acid. The locus containing the target nucleic acid can be constructed by a single transfection or multiple rounds of transfection with constructs containing different components of the locus.

In the embodiment, in which selection for a cell with a desired activity is indirect, the method of the invention further comprises (c) transfecting the cell from step (b) with a further genetic construct comprising a reporter gene capable of being influenced by the target nucleic acid.

In a further embodiment, the method of the invention further comprises (d) conditional expression of a trans-acting regulatory factor. In a preferred embodiment, the trans-acting regulatory factor is activation-induced deaminase (AID).

According to a particularly preferred embodiment, the target nucleic acid is inserted into the cell by targeted integration.

In a further aspect, there is provided a method for preparing a gene product having a desired activity, comprising the steps of: (a) culturing cells according to the invention under appropriate conditions to express the target nucleic acid, (b) identifying a cell or cells within the population of cells which expresses a mutated gene product having the desired activity; and (c) establishing one or more clonal populations of cells from the cell or cells identified in step (b), and selecting from said clonal populations a cell or cells which expresses a gene product having an improved desired activity.

In one embodiment, steps (b) and (c) are iteratively repeated until a gene product with an optimized desired activity is produced.

According to a further embodiment, the genetic diversification can be switched off, for example, by down-regulation of the expression of a trans-acting regulatory factor, when the cell producing a gene product with an optimized desired activity has been identified. The trans-acting regulatory factor can be, for example, activation-induced deaminase (AID) or a factor involved in homologous recombination or DNA repair, other than a RAD51 paralogue or analogue.

In another embodiment, the diversification of the target nucleic acid is further modified by target sequence optimization such as the introduction of Ig hypermutation hotspots or an increased GC content.

In a further aspect of the present invention, there is provided the use of a cell capable of directed and selective genetic diversification of a target nucleic acid by hypermutation or a combination of hypermutation and gene conversion for the preparation of a gene product having a desired activity.

DETAILED DESCRIPTION OF THE INVENTION

Figure 1:
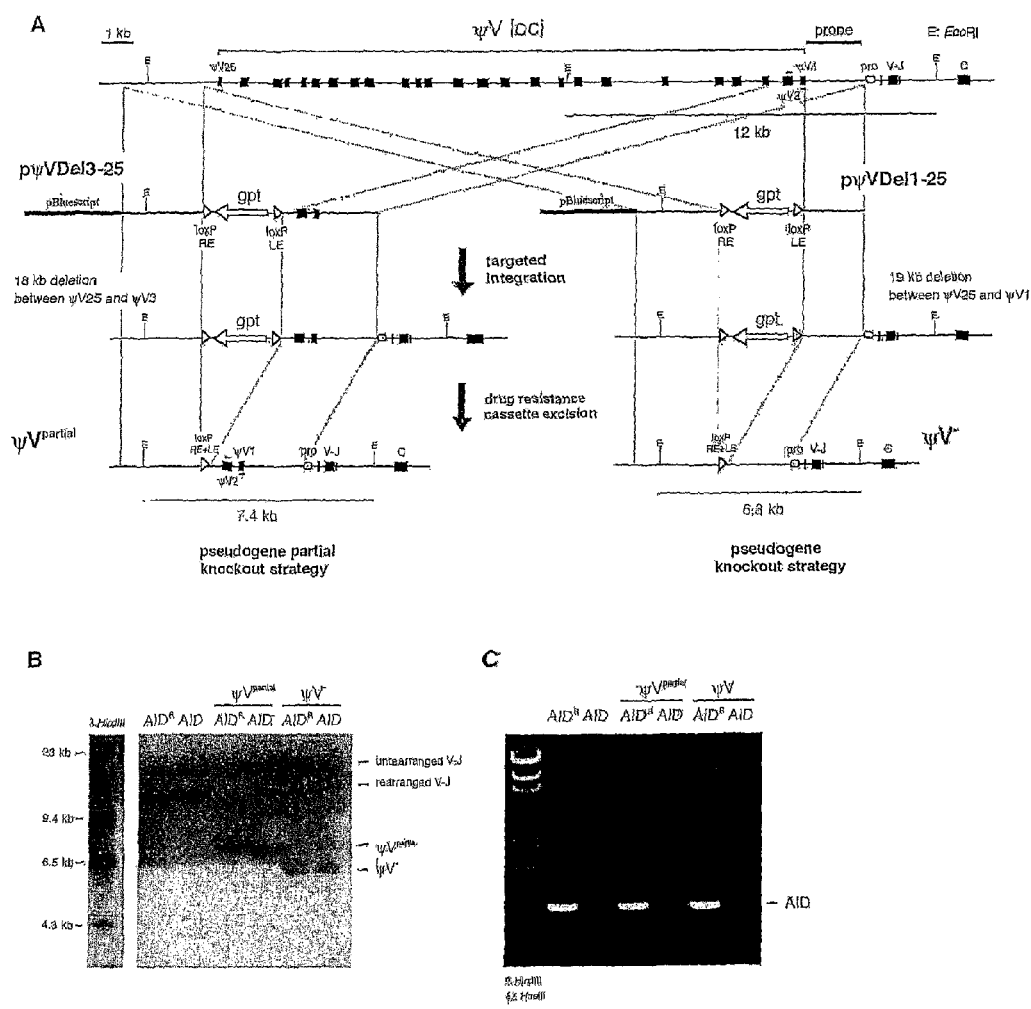
FIG. 1 ψN gene deletion (A) A physical map of the chicken rearranged Ig light chain locus and the ψV knock-out constructs. The locus contains a total of 25 ψV genes upstream of functional V segment. The knock-out strategy of ψV genes by the targeted integration of the pψVDel1-25 and the pψVDel3-25 constructs is shown below. Only the relevant EcoRI sites are indicated. (B) Southern blot analysis of wild-type and knock-out clones using the probe shown in (A) after EcoRI digestion. The wild-type locus hybridizes as a 12-kb fragment, whereas ψV$^{partial}$ and ψV$^-$ loci hybridize as a 7.4-kb and 6.3-kb fragment, respectively. (C) AID status. The AID gene was amplified by PCR to verify the presence or absence of AID cDNA expression cassette.

The present invention makes available a particularly useful cell system for directed and selective genetic diversification of any nucleic acid by hypermutation or a combination of hypermutation and gene conversion. The system is based on B cell lines which constitutively diversify the rearranged immunoglobulin V-gene in vitro without requiring extracellular stimuli such as an interaction with other cells or molecules or maintenance of the B cell antigen receptor.

As used herein, "directed and selective diversification" refers to the ability of certain cells to cause alteration of the nucleic acid sequence of a specific region of endogenous or transgenic nucleic acid, whereby sequences outside of these regions are not subjected to mutation.

"Genetic diversification" refers to alteration of individual nucleotides or stretches of nucleotides in a nucleic acid. Genetic diversification in the cells according to the invention occurs by hypermutation, gene conversion or a combination of hypermutation and gene conversion.

"Hypermutation" refers to the mutation of a nucleic acid in a cell at a rate above background. Preferably, hypermutation refers to a rate of mutation of between $10^{-5}$ and $10^{-3}$ bp$^{-1}$ generation$^{-1}$. This is greatly in excess of background mutation rates, which are of order of $10^{-9}$ to $10^{-10}$ mutations bp$^{-1}$ generation$^{-1}$ (Drake et al. 1988) and of spontaneous mutations observed in PCR. Thirty cycles of amplification with Pfu polymerase would produce $<0.05\times10^{-3}$ mutations bp$^{-1}$ in the product, which in the present case would account for less than 1 in 100 of the observed mutations (Lundberg et al., 1991).

"Gene conversion" refers to a phenomenon in which sequence information is transferred in unidirectional manner from one homologous allele to the other. Gene conversion may be the result of a DNA polymerase switching templates and copying from a homologous sequence, or the result of mismatch repair (nucleotides being removed from one strand and replaced by repair synthesis using the other strand) after the formation of a heteroduplex.

Hypermutation and gene conversion generate natural diversity within the immunoglobulin V(D)J segment of B cells. Hypermutation takes place in the germinal centers of such species as mouse and human following antigen stimulation. Gene conversion takes place in primary lymphoid organs like the Bursa of Fabricius or the gut-associated lymphoid tissue in such species as chicken, cow, rabbit, sheep and pig independent of antigen stimulation. In chicken, stretches from the upstream pseudo-V-genes are transferred into the rearranged V(D)J segment. According to the present invention, therefore, the cell or cell line is preferably an immunoglobulin-producing cell or cell line which is capable of diversifying its rearranged immunoglobulin genes.

A direct connection between the initiation of hypermutation and gene conversion is for the first time established in the experiments reported herein. Specifically, partial or complete deletion of pseudo-V-genes in a cell line which continues gene conversion in cell culture leads to the activation of hypermutation in the immunoglobulin locus. Deletion of all pseudogenes results in the abolishment of gene conversion and simultaneous activation of high rates of hypermutation, whereas deletion of a few pseudogenes results in the down-regulation of gene conversion and simultaneous activation of hypermutation at rates lower than the ones observed for the complete pseudogene deletion. Therefore, the number of available pseudogene donors directly correlates with gene conversion rates and inversely correlates with hypermutation rates. Gene conversion and hypermutation are established to be in a reciprocal relationship to each other. Thus, the present invention for the first time provides a cell system which allows to genetically diversify a target nucleic acid by a combination of hypermutation and gene conversion, whereby the contribution of these two phenomena can be regulated by changing the number of the gene conversion donors, their orientation or their degree or length of homology.

An advantage of the cell system according to the invention over a cell system with only hypermutating activity such as the one based on the human Burkitt lymphoma cell line Ramos (WO 00/22111 and WO 02/100998) is the ability to combine genetic diversification by hypermutation and gene conversion in one cell. For example, more defined changes can be introduced into the target gene by gene conversion than by random hypermutation, since gene conversion donors can be engineered to contain sequences likely to influence the target nucleic acid activity in a favorable way. Gene conversion and hypermutation might thus increase the chance to produce desirable variants, since pre-tested sequence blocks are combined with random hypermutations. Pseudogenes with sequences identical to a certain region of the target gene can also be used to keep a part of the target nucleic acid stable by frequent conversions having the effect that the hypermutations persist only in the non-converting part. This approach is useful when the target nucleic acid contains region which should remain stable for optimal activity.

An advantage of the cell system according to the invention over a cell system based on the suppression of homologous recombination activity in gene conversion active cells (WO 02/100998) is genetic stability of the cell reflected in a normal proliferation rate, radiation resistance and DNA repair competence.

A particular advantage of the present cell system over all known systems is the ability of the cells according to the invention to integrate transfected nucleic acid constructs by targeted integration into the homologous endogenous locus.

"Targeted integration" is integration of a transfected nucleic acid construct comprising a nucleic acid sequence homologous to an endogenous nucleic acid sequence by homologous recombination into the endogenous locus. Targeted integration allows to directly insert any nucleic acid into a defined chromosomal position. In a preferred embodiment, a nucleic acid encoding a gene product of interest is inserted by targeted integration into the immunoglobulin locus in place of the rearranged V(D)J segment or a portion thereof.

In a preferred embodiment, the cells according to the invention are derived or related to cells which undergo Ig gene conversion in vivo. Cells which undergo Ig gene conversion in vivo are, for example, surface Ig expressing B cells in primary lymphoid organs such as avian Bursal B cells. Lymphoma cells, derived from B cells of primary lymphoid organs, are particularly good candidates for constructing cells and cell lines according to the present invention. In the most preferred embodiment, the cells are derived from a chicken Bursal lymphoma cell line DT40.

The process of constitutive genetic diversification by hypermutation and gene conversion is used in the present invention to produce gene products with a desired, novel or improved, activity.

A "target nucleic acid" is a nucleic acid sequence or chromosomal region in the cell according to the present invention which is subjected to direct and selective genetic diversification. The target nucleic acid can be either endogenous or transgenic and may comprise one or more transcription units encoding gene products.

As used herein, a "transgene" is a nucleic acid molecule which is inserted into a cell, such as by transfection or transduction. For example, a transgene may comprise a heterologous transcription unit which may be inserted into the genome of a cell at a desired location.

In one embodiment, transgenes are immunoglobulin V-genes as found in immunoglobulin-producing cells or fragments of V-genes. Preferably, the target nucleic acid is a human immunoglobulin V-gene. In this case, the cells according to the invention are "factories" of human antibody variants capable of binding to any given antigen.

Alternatively, the target nucleic acid is a non-immunoglobulin nucleic acid, for example a gene encoding selection markers, DNA-binding proteins, enzymes or receptor proteins. For example, a novel fluorescent selection marker can be produced by mutating a known marker by hypermutation or by a combination of hypermutation and gene conversion with help of other known markers with a different fluorescent spectrum serving as gene conversion donors.

In one embodiment of the invention, the target nucleic acid directly encodes a gene product of interest. Gene diversification of such a nucleic acid will result in a truncation of the encoded gene product or in a change of its primary sequence. With every round of diversification and selection, a cell expressing the gene product with an improved activity is search for.

Alternatively, the target nucleic acid is a regulatory element, for example, a transcription regulatory element such as promoter or enhancer, or interfering RNA (RNAi). In this embodiment, an additional nucleic acid (reporter gene) which is influenced by the target nucleic acid and encodes an identifiable gene product is required to identify cells bearing the target nucleic acid of interest.

In the embodiment, in which genetic diversification of the target nucleic acid takes place by a combination of hypermutation and gene conversion, additional nucleic acids capable of serving as gene conversion donors are inserted into the cell genome, preferably upstream of the target nucleic acid.

A "nucleic acids capable of serving as a gene conversion donor" is a nucleic acid having a sequence homologous to the target nucleic acid. Examples of natural gene conversion donors are pseudo-V-genes in the immunoglobulin locus of certain species.

According to one embodiment of the invention, a cell capable of directed and selective diversification of the target nucleic acid is constructed by inserting the target nucleic acid into the host cell by targeted integration at a defined chromosomal site. For this purpose, the transfected constructs may contain upstream and downstream of the target nucleic acid sequences homologous to the desired chromosomal integration site. Preferably, the cell is constructed by replacing the endogenous V-gene or segments thereof with a transgene by homologous recombination, or by gene targeting, such that the transgene becomes a target for the gene conversion and/or hypermutation events.

In another embodiment, transgenes according to the invention also comprise sequences which direct hypermutation and/or gene conversion. Thus, an entire locus capable of expressing a gene product and directing hypermutation and gene conversion to this transcription unit is transferred into the cells and is actively diversified even after random chromosomal integration.

Screening of clones having incorporated the transgene by targeted integration can be done by Southern blot analysis or by PCR.

In a preferred embodiment, transgenes according to the invention contain a selectable marker gene which allows selection of clones which have stably integrated the transgene. This selectable marker gene may subsequently be removed by recombination or inactivated by other means.

The present invention further provides a method for preparing a gene product having a desired activity by repeated rounds of cell expansion and selection for cells bearing a target nucleic acid with a desired activity. As used herein, "selection" refers to the determination of the presence of sequence alterations in the target nucleic acid which result in a desired activity of the gene product encoded by the target nucleic acid or in a desired activity of the regulatory function of the target nucleic acid.

The process of gene conversion and hypermutation is employed in vivo to generate improved or novel binding specificities in immunoglobulin molecules. Thus, by selecting cells according to the invention which produce immunoglobulins capable of binding to the desired antigen and then propagating these cells in order to allow the generation of further mutants, cells which express immunoglobulins having improved binding to the desired antigen may be isolated.

A variety of selection procedures may be applied for the isolation of mutants having a desired specificity. These include Fluorescence Activated Cell Sorting (FACS), cell separation using magnetic particles, antigen chromatography methods and other cell separation techniques such as use of polystyrene beads.

Fluorescence Activated Cell Sorting (FACS) can be used to isolate cells on the basis of their differing surface molecules, for example surface displayed immunoglobulins. Cells in the sample or population to be sorted are stained with specific fluorescent reagents which bind to the cell surface molecules. These reagents would be the antigen(s) of interest linked (either directly or indirectly) to fluorescent markers such as fluorescein, Texas Red, malachite green, green fluorescent protein (GFP), or any other fluorophore known to those skilled in the art. The cell population is then introduced into the vibrating flow chamber of the FACS machine. The cell stream passing out of the chamber is encased in a sheath of buffer fluid such as PBS (Phosphate Buffered Saline). The stream is illuminated by laser light and each cell is measured for fluorescence, indicating binding of the fluorescent labeled antigen. The vibration in the cell stream causes it to break up into droplets, which carry a small electrical charge. These droplets can be steered by electric deflection plates under computer control to collect different cell populations according to their affinity for the fluorescent labeled antigen. In this manner, cell populations which exhibit different affinities for the antigen(s) of interest can be easily separated from those cells which do not bind the antigen. FACS machines and reagents for use in FACS are widely available from sources world-wide such as Becton-Dickinson, or from service providers such as Arizona Research Laboratories.

Another method which can be used to separate populations of cells according to the affinity of their cell surface protein(s) for a particular antigen is affinity chromatography. In this method, a suitable resin (for example CL-600 Sepharose, Pharmacia Inc.) is covalently linked to the appropriate antigen. This resin is packed into a column, and the mixed population of cells is passed over the column. After a suitable period of incubation (for example 20 minutes), unbound cells are washed away using (for example) PBS buffer. This leaves only that subset of cells expressing immunoglobulins which bound the antigen(s) of interest, and these cells are then eluted from the column using (for example) an excess of the antigen of interest, or by enzymatically or chemically cleaving the antigen from the resin. This may be done using a specific protease such as factor X, thrombin, or other specific protease known to those skilled in the art to cleave the antigen from the column via an appropriate cleavage site which has previously been incorporated into the antigen-resin complex. Alternatively, a non-specific protease, for example trypsin, may be employed to remove the antigen from the resin, thereby releasing that population of cells which exhibited affinity for the antigen of interest.

The present invention provided for the first time a mechanism which allows to regulate genetic diversification of the target nucleic acid. As demonstrated by the present inventors, activation-induced deaminase (AID) is a factor which regulates gene conversion as well as hypermutation in the immunoglobulin locus. It is suggested that AID induces a common modification in the rearranged V(D)J segment leading to a conversion tract in the presence of adjacent donor sequences and to a point mutation in their absence. Therefore, by regulation of AID expression, both phenomena can be modulated. In a preferred embodiment, the AID gene is transiently expressed in the cell containing a target nucleic acid. For example, AID can be expressed under a drug-responsive promoter such as the tetracycline responsible gene expression system. Otherwise the gene expression may be shut down by the excision of the AID expression cassette by induced recombination. Switching off the AID expression will prevent further diversification of the target sequence. Preferably, AID expression is switched off in the cell producing a gene product with a desired activity in order to prevent further mutations which can lead to the loss of the desired activity.

The invention is illustrated by the following examples.

EXAMPLES

1. AID Initiates Immunoglobulin Gene Conversion and Hypermutation by a Common Intermediate Herein it is reported that ablation of ψV donors activates AID-dependent Ig hypermutation in chicken B cell line DT40. This shows that Ig gene conversion and hypermutation are competing pathways derived from the same AID-initiated intermediate. Furthermore ψV knock-out DT40 is proposed as an ideal model system to approach the molecular mechanism of Ig hypermutation and as a new tool for in situ mutagenesis.

Methods

Cell lines. $DT40^{Cre1}$ which displays increased Ig gene conversion due to a v-myb transgene and contains a tamoxifen inducible Cre recombinase has been described previously (Arakawa et al., 2001). $DT40^{Cre1}$ $AID^{-/-}$ was generated by the targeted disruption of both AID alleles of $DT40^{Cre1}$ (Arakawa et al., 2002). $AID^R$ was derived from $DT40^{Cre1}$ $AID^{-/-}$ after stable integration of a floxed AID-IRES-GFP bicistronic cassette, in which both AID and GFP are expressed from the same β-actin promoter. $AID^R\psi V^-$ was derived from $AID^R$ by transfection of pψVDel1-25 (FIG. 1A). Stable transfectants which had integrated the construct into the rearranged light chain locus were then identified by locus specific PCR. Targeted integration of pψVDel1-25 results in the deletion of the entire ψV gene loci starting 0.4 kb upstream of ψV25 and ending one bp downstream of ψV1. $AID^R\psi V^{partial}$ was produced in a similar way as $AID^R\psi V^-$ by transfection of pψVDel3-25 which upon targeted integration leads to a partial deletion of the ψV loci starting 0.4 kb upstream of ψV25 and ending one bp downstream of ψV3. Cell culture and electroporation were performed as previously described (Arakawa et al., 2002). $XRCC3^{-/-}$ was derived from $DT40^{Cre1}$ by deleting amino acids 72-170 of XRCC3 gene following transfection of XRCC3 knock-out constructs. Clones having undergone targeted integration were initially identified by long-range PCR and the XRCC3 deletion was then confirmed by Southern blot analysis.

Ig reversion assay. Subcloning, antibody staining, flow cytometry and quantification of sIgM expression has been described previously (Arakawa et al., 2002). All clones used in the study were sIgM(+) due to the repair of the light chain frameshift of the original C118(−) variant (Buerstedde et al., 1990) by a gene conversion event.

PCR. To minimize PCR-introduced artificial mutations, PfuUltra hotstart polymerase (Stratagene) was used for amplification prior to sequencing. Long-range PCR, RT-PCR and Ig light chain sequencing were performed as previously described (Arakawa et al., 2002). The promoter and J-C intron region of Ig light chain plasmid clones were sequenced using the M13 forward and reverse primers. Bu-1 and EF1α genes were amplified using BU1/BU2 (BU1, GGGAAGCT-TGATCATTTCCTGAATGCTATATTCA (SEQ ID NO: 13); BU2, GGGTCTAGAAACTCCTAGGG-GAAACTTTGCTGAG (SEQ ID NO: 14)) and EF6/EF8

(EF6, GGGAAGCTTCGGAAGAAAGAAGCTAAA-GACCATC (SEQ ID NO: 15); EF8, GGGGCTAGCAGAA-GAGCGTGCTCACGGGTCTGCC (SEQ ID NO: 16)) primer pairs, respectively. The PCR products of these genes were cloned into the pBluescript plasmid vector, and were sequenced using the M13 reverse primer.

Results

Targeted Deletion of ψV Donor Sequences in the Rearranged Light Chain Locus

Two ψV knock-out constructs were made by cloning genomic sequences, which flank the intended deletion end points, upstream and downstream of a floxed-gpt (guanine phosphoribosyl transferase) cassette (Arakawa et al., 2001). Upon targeted integration, the first construct, pψVDel1-25, deletes all pseudogenes (ψV25 to ψV1) whereas the second construct, pψVDel3-25, deletes most pseudogenes (ψV25 to ψV3) (FIG. 1A). A surface IgM positive (sIgM(+)) clone, derived from DT40$^{Cre1}$ AID$^{-/-}$ cells (Arakawa et al., 2002) by transfection and stable integration of a floxed AID-IRES (internal ribosome entry site)-GFP transgene, was chosen for the transfection of the ψV knock-out constructs. This AID reconstituted clone, named AID$^R$, has the advantage that the appearance of deleterious Ig light chain mutations can be easily detected by the loss of sIgM expression and that GFP-marked AID expression can be shut down after tamoxifen induction of the Cre recombinase transgene inherited from DT40$^{Cre1}$ (Arakawa et al., 2002).

Following transfection of the ψV knock-out constructs into the AID$^R$ clone, mycophenolic acid resistant clones containing targeted deletions of the rearranged light chain locus were identified. These primary ψV knock-out clones contain two floxed transgenes, the inserted gpt marker gene in the rearranged light chain locus and the AID-IRES-GFP gene of the AID$^R$ progenitor clone. Since the gpt gene might perturb the adjacent transcription or chromatin configuration, the primary ψV knock-outs were exposed to a low concentration of tamoxifen and then subcloned by limited dilution. In this way, secondary ψV knock-out clones could be isolated which had either deleted only the gpt gene (AID$^R$ψV$^-$ and AID$^R$ψV$^{partial}$) or the gpt gene together with the AID-IRES-GFP gene (AID$^{-/-}$ψV$^-$ and AID$^{-/-}$ψV$^{partial}$). The disruption of ψV genes in the rearranged light chain locus and the excision of AID over-expression cassette were confirmed by Southern blot analysis (FIG. 1B) and PCR (FIG. 1C), respectively.

Figure 2:
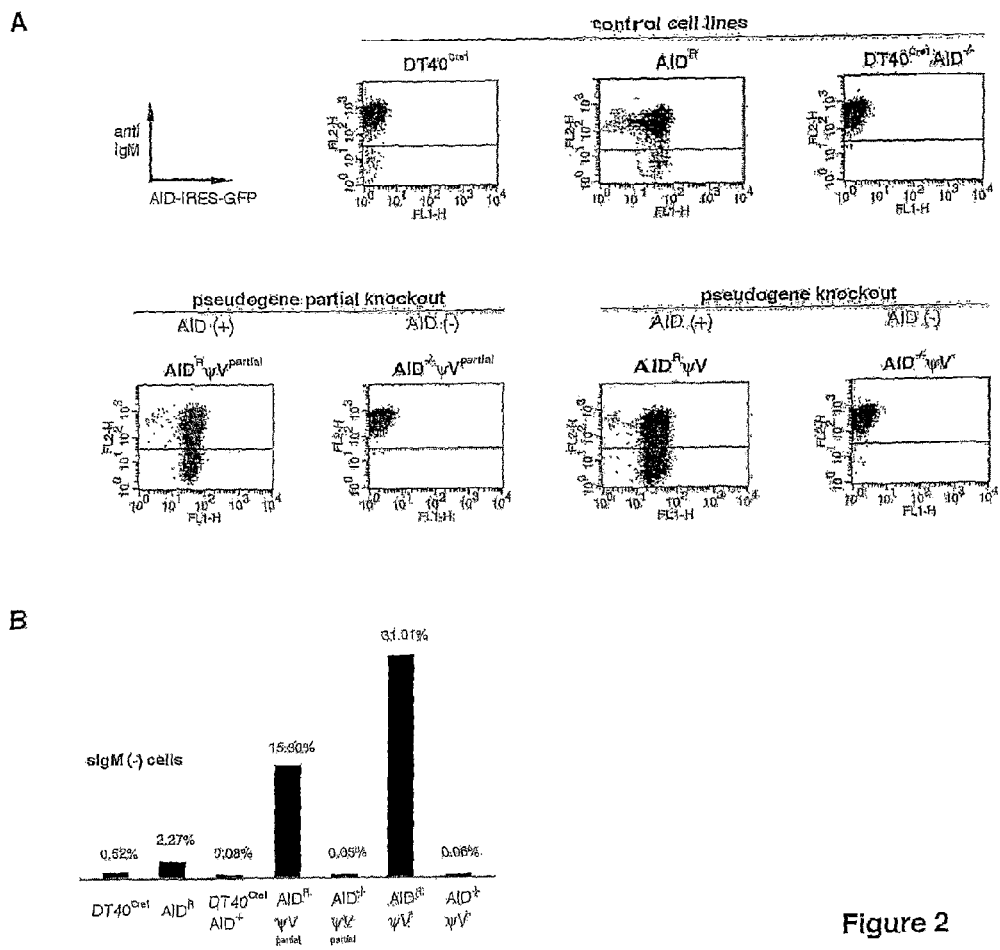
FIG. 2 sIgM expression analysis of control and ψV knock-out clones (A) FACS anti-IgM staining profiles of representative subclones derived from initially sIgM(+) clones. (B) Average percentages of events falling into sIgM(−) gates based on the measurement of 24 subclones.

Increased Loss of sIgM Expression after Deletion of ψV Genes in AID Positive Clones To estimate the rates of deleterious Ig mutations, sIg expression was measured by FACS after two weeks culture for 24 subclones each of the DT40$^{Cre1}$, AID$^R$, DT40$^{Cre1}$ AID$^{-/-}$ and ψV knock-out clones (FIGS. 2A and 2B). Analysis of the controls with the intact ψV locus revealed an average of 0.52% and 2.27% sIgM(-) cells for the DT40$^{Cre1}$ and AID$^R$ subclones respectively, but only 0.08% for the DT40$^{Cre1}$ AID$^{-/-}$. Previous analysis of spontaneously arising sIgM(-) DT40 variants demonstrated that about a third contained frameshift mutations in the rearranged light chain V segment which were regarded as byproducts of the Ig gene conversion activity (Buerstedde et al., 1990). This view is now supported by the finding that the AID negative DT40$^{Cre1}$ AID$^{-/-}$ clone, which should have lost the Ig gene conversion activity, stably remains sIgM(+). Most interestingly, subclones of the AID positive ψV knock-out clones (AID$^R$ψV$^{partial}$ and AID$^R$ψV$^-$) rapidly accumulate sIgM(-) populations whereas subclones of the AID negative ψV knock-out clones (AID$^{-/-}$ψV$^{partial}$ and AID$^{-/-}$ψV$^-$) remain sIgM(+) (FIGS. 2A and 2B). This suggests that the deletion of the pseudogenes dramatically increases the rate of deleterious light chain mutations in AID expressing cells.

Replacement of Ig Gene Conversion by Hypermutation in the Absence of ψV Donors

Figure 3:
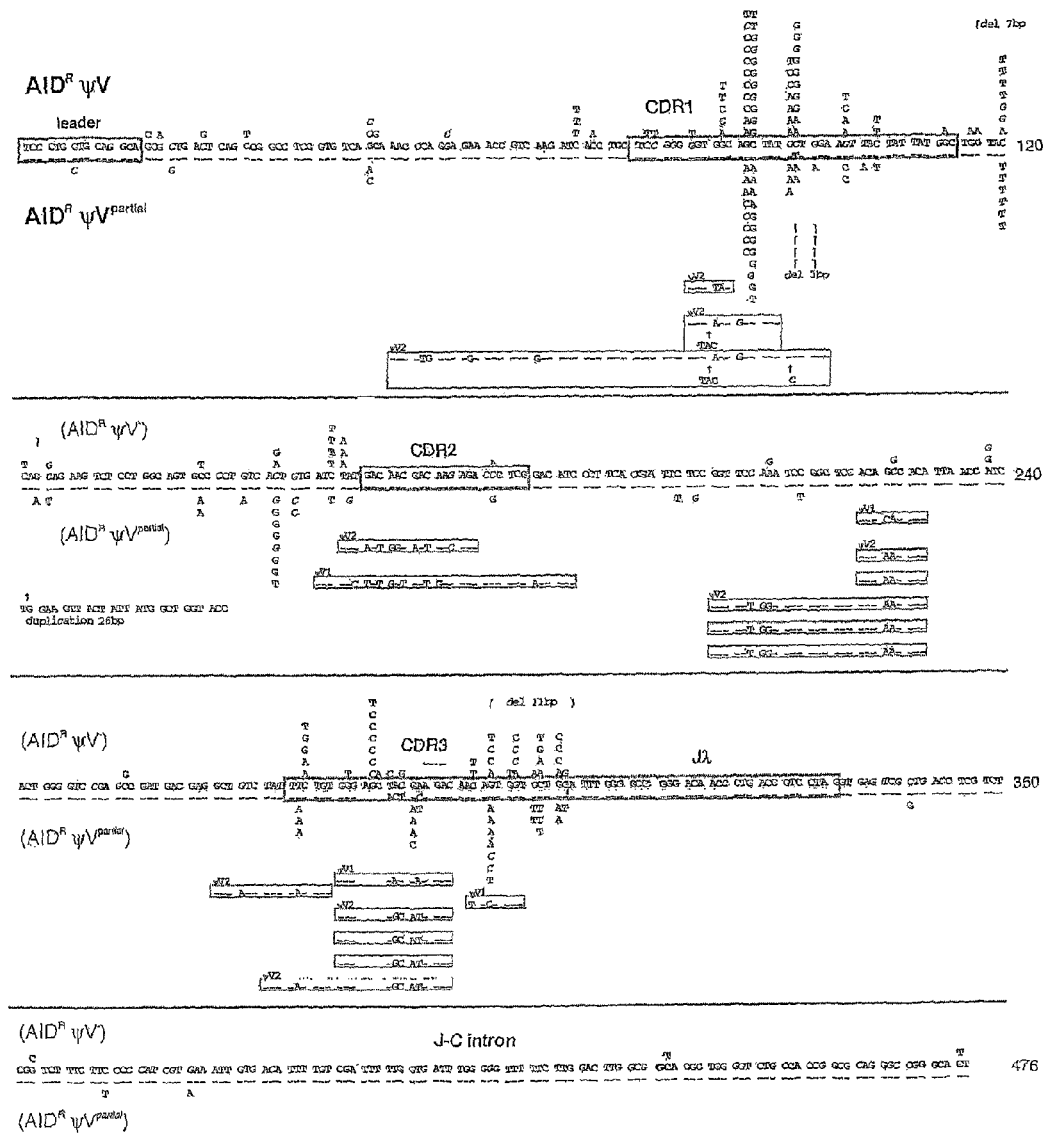
FIG. 3 Ig light chain sequence analysis of the ψV knock-out clones Mutation profiles of the AID$^R$ωV$^-$ (SEQ ID NO: 1) and AID$^R$ψV$^{partial}$ (SEQ ID NO: 2) clones. All nucleotide substitutions identified in different sequences in the region from the leader sequence to the J-C intron are mapped onto the rearranged light chain sequence present in the AID$^R$ precursor clone. Mutations of the AID$^R$ψV$^-$ and the AID$^R$ψV$^{partial}$ clones are shown above and below the reference sequence, respectively. Deletions, insertions and gene conversion events are also indicated. Hotspot motifs (RGYW and its complement WRCY) are highlighted by bold letters.

To analyze the newly identified mutation activity, the rearranged light chain VJ segments of the ψV knock-out clones were sequenced 5-6 weeks after subcloning. A total of 135 nucleotide changes (FIG. 4A, Table 1) were found in the 0.5 kb region between the V leader and the 5' end of the J-C intron within 95 sequences from the AID$^R$ψV$^-$ clone (FIG. 3, above reference sequence). In contrast to the conversion tracts seen in wild-type DT40 cells, almost all changes are single base substitutions and apart from a few short deletions and di-nucleotide changes, mutation clusters were not observed. The lack of conversion events in AID$^R$ψV$^-$, which still contains the ψV genes of the on rearranged light chain locus, confirms that Ig gene conversion only recruits the ψV genes on the same chromosome for the diversification of the rearranged light chain gene (Carlson et al., 1990). No sequence diversity was found in a collection of 95 light chain gene sequences from the AID$^{-/-}$ψV$^-$ clone (FIG. 4A, Table 1), indicating that AID is required for the mutation activity.

Figure 4:
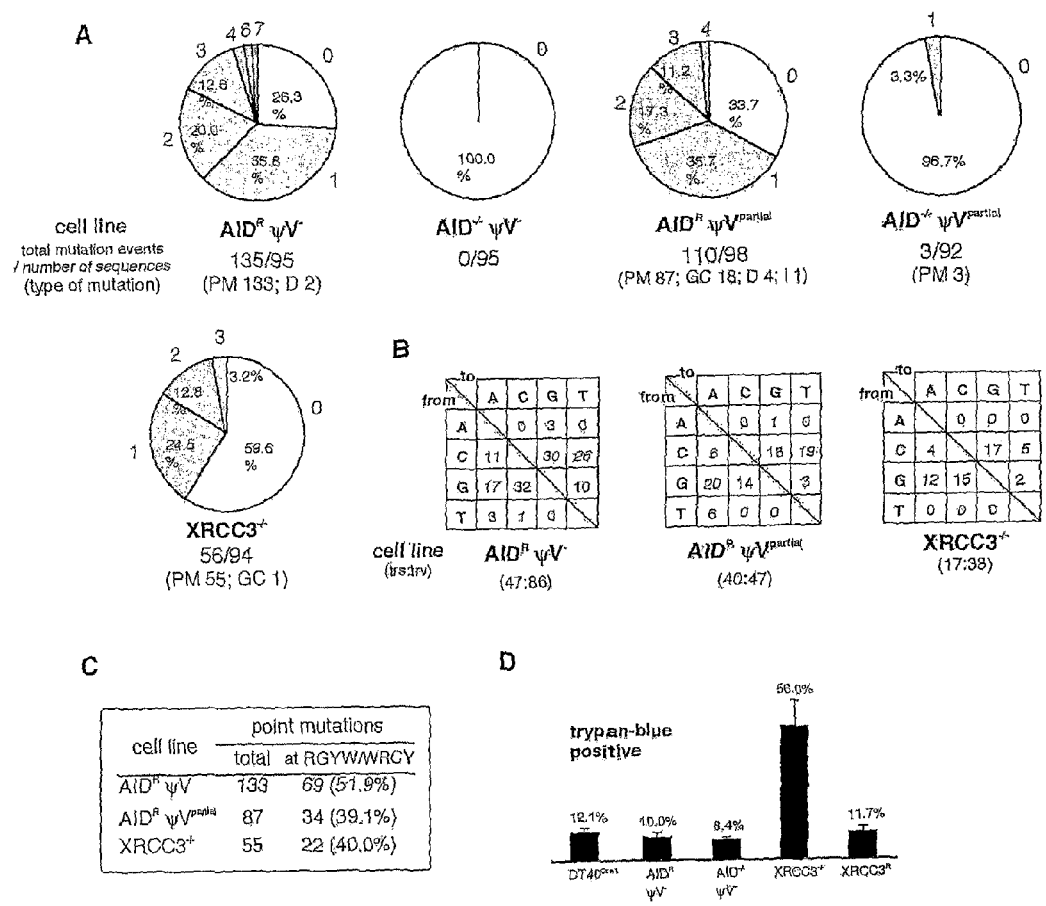
FIG. 4 Mutation profiles of hypermutating cell lines (A) Percentages of sequences carrying a certain number of mutations. Each untemplated nucleotide substitution is counted, but gene conversion, deletions and insertions involving multiple nucleotides are counted as a single event. PM, point mutation; GC, gene conversion; D, deletion; I, insertion. (B) Pattern of nucleotide substitutions within sequences from ψV and the XRCC3 knock-out clones. Nucleotide substitutions as part of gene conversion events are excluded. The ratios of transition (trs) to transversion (try) are also shown. (C) Hotspot preference of untemplated nucleotide substitution mutations. Mutations occurring within a hotspot motif (RGYW or its complement WRCY) are shown by percentages. (D) Trypan-blue positive cells as an indicator of spontaneously dying cells.

Sequences derived from the AID$^R$ψV$^{partial}$ clone occasionally display stretches of mutations which can be accounted for by the remaining ψV1 and ψV2 (FIG. 3, below reference sequence). Nevertheless, the majority of AID$^R$ψV$^{partial}$ mutations are single untemplated base substitutions as seen with the AID$^R$ψV$^-$ cells (FIG. 4A, Table 1). Only 3 base substitutions, which possibly are PCR artifacts, were found in 92 sequences of the AID$^{-/-}$ψV$^{partial}$ clone confirming that both the gene conversion and the mutation activities of AID$^R$ψV$^{partial}$ are AID dependent.

The New Mutation Activity of the ψV Knock-Out Clones Closely Resembles Somatic Hypermutation The discovered Ig mutation activity in the ψV knock-out clones with a predominance of single nucleotide substitutions suggests that somatic hypermutation had replaced Ig gene conversion. There is however a difference between the nucleotide substitutions in the AID$^R$ψV$^{partial}$ and AID$^R$ψV$^-$ clones and Ig hypermutations in germinal center B cells in that the clones show very few mutations in A/T bases and a preference for transversion mutations (FIG. 4B).

Figure 5:
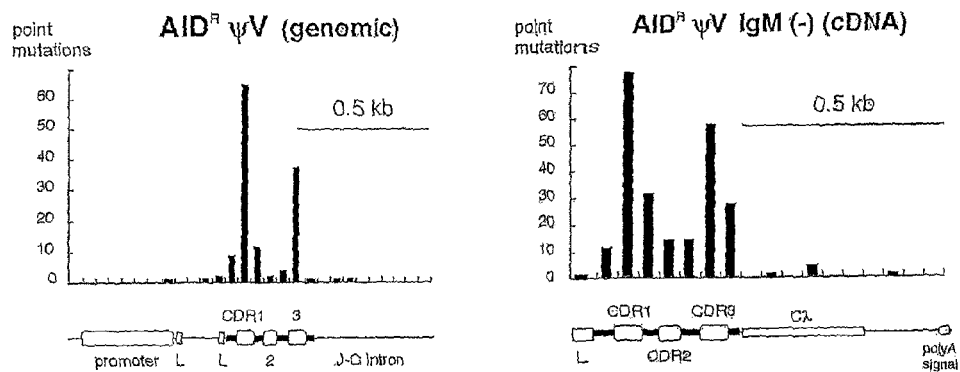
FIG. 5 Distribution of nucleotide substitutions within genomic sequences from unsorted AID$^R$ψV$^-$ cells and within cDNA sequences from sorted IgM (−) AID$^R$ψV$^-$ cells. The number of mutations are counted for every 50 bp, and are shown together with the corresponding physical maps of the light chain genomic locus or the cDNA sequence.

Ig hypermutations are typically localized within one kb of the transcribed gene sequence with preferences for the Complementary Determining Regions (CDRs) of the V(D)J segments, whereas no or few mutations are present in the downstream C region (Lebecque and Gearhart, 1990). To investigate whether the mutations in the AID$^R$ψV$^-$ clone follow a similar distribution, sequence analysis was extended to the promoter region and the J-C intron of the rearranged light chain gene (FIG. 5). Although mutations are found close to the promoter and in the intron downstream of the J segments, the peak incidence clearly coincides with the CDR1 and CDR3, which are also preferred sites of gene conversion in DT40 (unpublished results). Approximately half of all point mutations fall within the RGYW (R=A/G; Y=C/T; W=A/T) sequence motif or its complement WRCY (FIG. 4C), known as hot spots of Ig hypermutation in humans and mice.

It was previously reported that the deletion of RAD51 paralogues induces Ig hypermutation in DT40 (Sale et al., 2001). To compare the hypermutation activity in the ψV gene negative and RAD51 paralogue negative backgrounds, the XRCC3 gene was disrupted in the DT40$^{Cre1}$ clone and the rearranged VJ genes were sequenced 6 weeks after subcloning. Similar to the mutation spectrum in the AID$^R$ψV$^-$ clone and what was previously reported (Sale et al., 2001), the mutations in the sequences from the XRCC3$^{-/-}$ cells show a transversion preference and an absence of mutations in A/T bases (FIG. 4B). Nevertheless the mutation rate in the XRCC3 mutant was about 2.5 fold lower than in the AID$^R$ψV$^-$ clone and there was a clear slow growth phenotype of the XRCC3 mutant compared to wild-type DT40 and the AID$^R$ψV$^-$ clone (FIG. 4D).

To identify the mutations responsible for the loss of sIgM expression in the AID$^R$ψV$^-$ clone, 94 light chain cDNAs from sorted sIgM(-) cells were amplified and sequenced. Although one short insertion and five deletions were detected in this collection (Table 1), 89% of the 245 total mutations are single nucleotide substitutions within the VJ segments (FIG. 5). Surprisingly, only about 10% of the sequences contained a stop codon or a frameshift, suggesting that the lack of sIgM (-) expression is mainly caused by amino acid substitutions which affect the pairing of the Ig light and heavy chain proteins.

Ig Locus Specificity of Hypermutation

It has been reported that high AID expression in fibroblasts (Yoshikawa et al., 2002) and B cell hybridomas (Martin and Scharff, 2002) leads to frequent mutations in transfected transgenes. To rule out that the pseudogene deletions had induced a global hypermutator phenotype, the 5' ends of the genes encoding the B cell specific marker Bu-1 and the translation elongation factor EF1α were sequenced for the AID$^R$ψV$^-$ clone. Only a single one bp deletion was found within 95 sequences of the Bu-1 gene and only two single nucleotide substitutions within 89 sequences of EF1α (Table 1). As these changes most likely represent PCR artifacts, this further supports the view that the hypermutations induced by the ψV deletions are Ig locus specific.

Discussion

The results demonstrate that the deletion of the nearby pseudogene donors abolishes Ig gene conversion in DT40 and activates a mutation activity which closely resembles Ig hypermutation. The features shared between the new activity and somatic hypermutation include 1) AID dependence, 2) a predominance of single nucleotide substitutions, 3) distribution of the mutations within the 5' transcribed region, 4) a preference for hotspots and 5) Ig gene specificity. The only difference with regard to Ig hypermutation in vivo is the relative lack of mutations in A/T bases and a predominance of transversion mutations in the ψV knock-out clones. However, this difference is also seen in hypermutating EBV transformed B cell lines (Bachl and Wabl, 1996; Faili et al., 2002) and DT40 mutants of RAD51-paralogues (Sale et al., 2001) indicating that part of the Ig hypermutator activity is missing in transformed B cell lines. Interestingly, the rate of Ig hypermutation in the AID$^R$ψV$^-$ clone seems higher than the rate of Ig gene conversion in the DT40$^{Cre1}$ progenitor. An explanation for this could be that some conversion tracts are limited to stretches of identical donor and target sequences and thus leave no trace.

Figure 6:
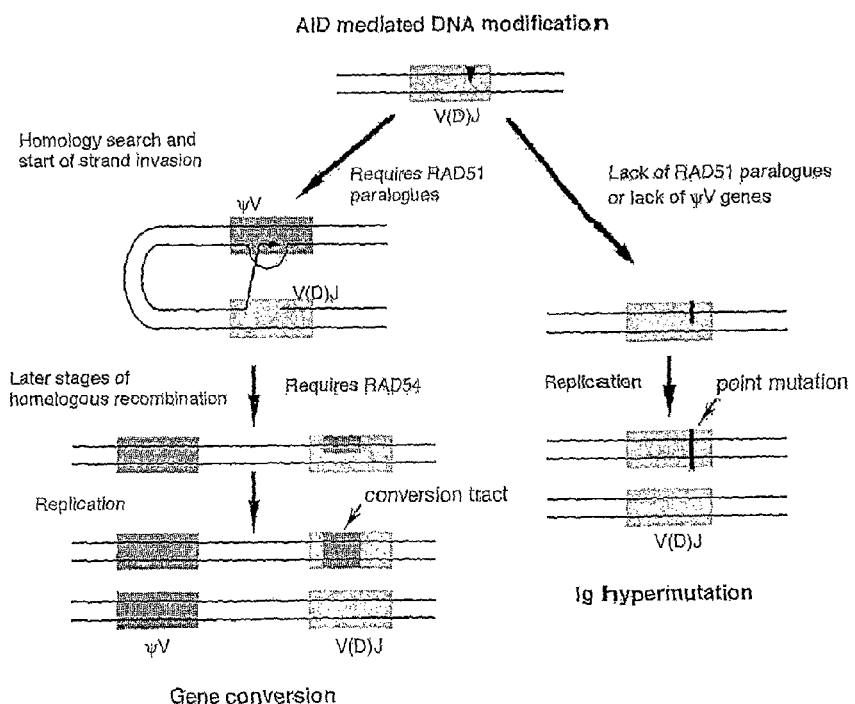
FIG. 6 A model explaining the regulation of Ig gene conversion and Ig hypermutation FIG. 7 In situ mutagenesis of the GFP gene (A) Ig VJ replacement vector. (B) in vivo mutagenesis of the GFP gene by hypermutation. (C) ψV donor replacement vector. (D) in vivo mutagenesis of GFP gene by gene conversion and hypermutation.

The induction of Ig hypermutation by the blockage of Ig gene conversions supports a simple model explaining how hypermutation and recombination is initiated and regulated (FIG. 6). At the top of the events is a modification of the rearranged V(D)J segment which is either directly or indirectly induced by AID. The default processing of this lesion in the absence of nearby donors or in the absence of high homologous recombination activity leads to Ig hypermutation in form of a single nucleotide substitution (FIG. 6, right side). However, if donor sequences are available, processing of the AID induced lesion can be divided into a stage before strand exchange, when a shift to Ig hypermutation is still possible and a stage after strand exchange when the commitment toward Ig gene conversion has been made (FIG. 6, left side). Whereas completion of the first stage requires the participation of the RAD51 paralogues, the second stage involves other recombination factors like the RAD54 protein.

This difference in commitment explains why disruptions of the RAD51 paralogues not only decrease Ig gene conversion, but also induce Ig hypermutation (Sale et al., 2001) whereas disruption of the RAD54 gene only decreases Ig gene conversion (Bezzubova et al., 1997). The model also predicts that low cellular homologous recombination activity prevents Ig gene conversion even in the presence of conversion donors. Such a low homologous recombination activity might be the reason why human and murine B cells never use Ig gene conversion despite the presence of nearby candidate donors in form of unrearranged V segments and why chicken germinal center B cells shave shifted from Ig gene conversion to Ig hypermutation (Arakawa et al., 1998).

The AID$^R$ and the ψV knock-out DT40 clones are a powerful experimental system to address the role of trans-acting factors and cis-acting regulatory sequences for Ig gene conversion and hypermutation. Compared to alternative animal or cell culture systems it offers the advantages of: 1) parallel analysis of Ig gene conversion and Ig hypermutation, 2) conditional AID expression, 3) easy genome modifications by gene targeting, 4) normal cell proliferation and repair proficiency and 5) Ig locus specificity of hypermutation. The ability to induce gene specific hypermutation in the DT40 cell line might also find applications in biotechnology. One possibility is to replace the chicken antibody coding regions by their human counterparts and then to simulate antibody affinity maturation from a repertoire which continuously evolves by Ig hypermutation.

2. Targeted In Vivo Mutagenesis of GFP by Gene Conversion and Hypermutation

Figure 7:
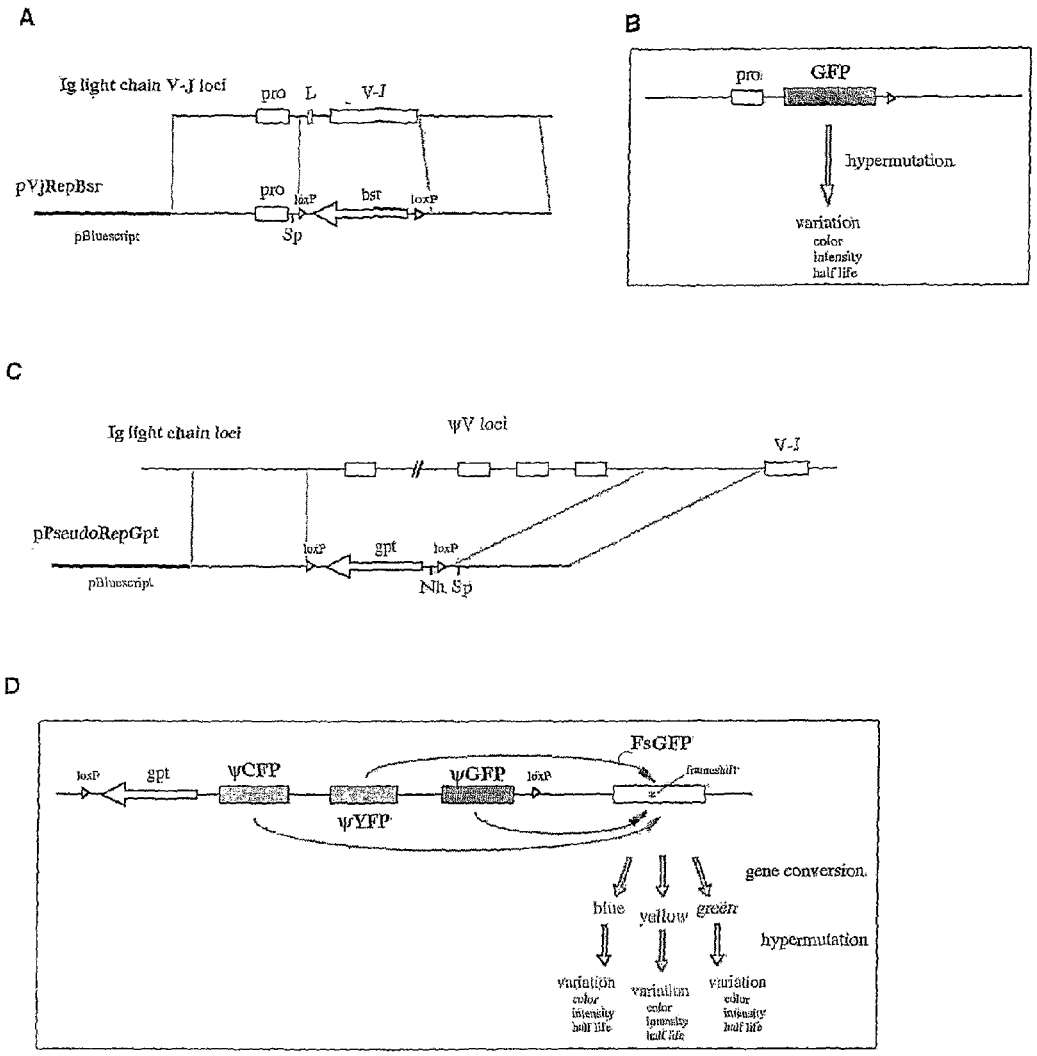

The gene encoding Green Fluorescent Protein (GFP) is an example of a target nucleic acid which can be genetically diversified using the cell system of the invention, in particular the DT40 cell line. The GFP gene inserted into the Ig light chain locus by targeted integration will be subjected to hypermutation and its activity with respect to color, intensity and half-life will evolve with time (FIG. 7B). If a combination of hypermutation and gene conversion is used to modify the GFP activities, variant GFP sequences which can serve as gene conversion donors for GFP are also inserted into the Ig locus (FIG. 7D).

An Ig VJ replacement vector, pVjRepBsr, which allows to replace the Ig light chain VJ gene by any nucleic acid target is depicted in FIG. 7A. A potential target for mutagenesis can be cloned into SpeI site, which is compatible with XbaI, NheI, AvrII and SpeI sites. For example, the GFP gene can be inserted into the Ig light chain locus by targeted integration using pVjRepBsr. A ψV-gene donor replacement vector, pPseudoRepBsr, which allows to replace the Ig ψV gene light chain locus by any nucleic acid target is depicted in FIG. 7C. Potential gene conversion donors can be cloned into either NheI or SpeI site, which is compatible with XbaI, NheI, AvrII and SpeI sites. Because NheI site is located between two loxPs, this site can be used for conditional knockout design. By stepwise targeted integration using pPseudoRepGpt and pVjRepBsr, ψV genes can be replaced by ψGFP gene and its variants (e.g. ψCFP: cyano fluorescence protein and ψYFP: yellow fluorescence protein) and the VJ gene can be replaced by GFP carrying a frameshift mutation (FsGFP) to monitor genetic diversification of the GFP gene. The frameshift in FsGFP is expected to be repaired by gene conversion of ψGFP, ψCFP and ψYFP as templates. In addition, the gene will be further diversified by hypermutation.

REFERENCES

1. Milstein, C. & Rada C. *Immunoglobulin genes* (Academic Press, London, ed. 2, 1995), pp. 57-81.
2. Butler, J. E. Immunoglobulin diversity, B-cell and antibody repertoire development in large farm animals. *Rev. Sci. Tech.* 17, 43-70 (1998).
3. Reynaud, C-A., Anquez, V., Grimal, H. & Weill, J-C. A hyperconversion mechanism generates the chicken light chain preimmune repertoire. *Cell* 48, 379-388 (1987).
4. Arakawa, H. & Buerstedde, J-M. Immunoglobulin Gene Conversion: Insights from Bursal B Cells and the DT40 Cell Line. *Dev. Dynamics*, in press.
5. Arakawa, H., Furusawa, S., Ekino, S. & Yamagishi, H. Immunoglobulin gene hyperconversion ongoing in chicken splenic germinal centers. *EMBO J.* 15, 2540-2546 (1996).
6. Arakawa, H., Hauschild, J. & Buerstedde, J-M. Requirement of the Activation-Induced Deaminase (AID) Gene for Immunoglobulin Gene Conversion. *Science* 295, 1301-1306 (2002).
7. Muramatsu, M. et al. Class switch recombination and hypermutation require activation-induced cytidine deaminase (AID), a potential RNA editing enzyme. *Cell* 102, 553-563 (2000).
8. Revy, P. et al. Activation-induced cytidine deaminase (AID) deficiency causes the autosomal recessive form of the Hyper-IgM syndrome. *Cell* 102, 565-575 (2000).
9. Muramatsu, M. et al. Specific expression of activation-induced cytidine deaminase (AID), a novel member of the RNA-editing, deaminase family in germinal center B cells. *J. Biol. Chem.* 274, 18470-18476 (1999).
10. Di Noia, J. & Neuberger, M. S. Altering the pathway of immunoglobulin hypermutation by inhibiting uracil-DNA glycosylase. *Nature* 419, 43-48 (2002).
11. Ta V. T. et al. AID mutant analyses indicate requirement for class-switch-specific cofactors. *Nat. Immunol.* 4, 843-848 (2003).
12. Barreto, V., Reina-San-Martin, B., Ramiro, A. R., McBride, K. M. & Nussenzweig M. C. C-terminal deletion of AID uncouples class switch recombination from somatic hypermutation and gene conversion. *Mol. Cell* 12, 501-508 (2003).
13. Bezzubova, O., Silbergleit, A., Yamaguchi-Iwai, Y., Takeda, S. & Buerstedde, J-M. Reduced X-ray resistance and homologous recombination frequencies in a RAD54-/- mutant of the chicken DT40 cell line. *Cell* 89, 185-193 (1997).
14. Sale, J. E., Calandrini, D. M., Takata, M., Takeda, S. & Neuberger, M. S. Ablation of XRCC2/3 transforms immunoglobulin V gene conversion into somatic hypermutation. *Nature* 412, 921-926 (2001).
15. Arakawa, H., Lodygin D. & Buerstedde J-M. Mutant loxP vectors for selectable marker recycle and conditional knock-outs. *BMC Biotechnology* 1, 7 (2001).
16. Buerstedde, J-M. et al. Light chain gene conversion continues at high rate in an ALV-induced cell line. *EMBO J.* 9, 921-927 (1990).
17. Carlson, L. M., McCormack, W. T., Postema, C. E., Humphries, E. H. & Thompson, C. B. Templated insertions in the rearranged chicken IgL V gene segment arise by intrachromosomal gene conversion. *Genes Dev.* 4, 536-547 (1990).
18. Lebecque, S. G. & Gearhart, P. J. Boundaries of somatic mutation in rearranged immunoglobulin genes: 5' boundary is near the promoter, and 3' boundary is approximately 1 kb from V(D)J gene. *J. Exp. Med.* 172, 1717-1727 (1990).
19. Yoshikawa, K. et al. AID enzyme-induced hypermutation in an actively transcribed gene in fibroblasts. *Science* 296, 2033-2036 (2002).
20. Martin, A. & Scharff, M. D. Somatic hypermutation of the AID transgene in B and non-B cells. *Proc. Natl. Acad. Sci. USA* 99, 12304-12308 (2002).
21. Bachl, J. & Wabl, M. An immunoglobulin mutator that targets G.C base pairs. *Proc. Natl. Acad. Sci. USA* 93, 851-855 (1996).
22. Faili, A. et al. AID-dependent somatic hypermutation occurs as a DNA single-strand event in the BL2 cell line. *Nat. Immunol.* 3, 815-821 (2002).
23. Arakawa, et al. Oligoclonal development of B cells bearing discrete Ig chains in chicken single germinal centers. *J. Immunol.* 160, 4232-4241 (1998).
24. Drake, J. W. *Genetics* 148, 1667-1686 (1998).
25. Lundberg, K. S. et al. *Gene* 108, 1-6 (1991).
26. Buerstedde, J. M. & Takeda, S. Increased ratio of targeted to random integration after transfection of chicken B cell lines. *Cell* Oct. 4, 67(1):179-88 (1991).

The invention claimed is:

1. A method for producing a hypermutated transgenic target nucleic acid sequence comprising
   a) transfecting a chicken immunoglobulin expressing B lymphoid cell with a genetic construct comprising a target nucleic acid sequence flanked by nucleic acid sequences homologous to an endogenous V gene immunoglobulin locus;
   b) integrating said genetic construct comprising said target nucleic acid sequence into said endogenous V gene immunoglobulin locus of said chicken immunoglobulin expressing B lymphoid cell, wherein said chicken immunoglobulin expressing B lymphoid cell comprises a functional activation-induced deaminase (AID) protein, and functional XRCC2, XRCC3, and RAD51 proteins or their analogues; and
   c) culturing said chicken immunoglobulin expressing B lymphoid cell transgenic for said target nucleic acid to produce said hypermutated transgenic target nucleic acid sequence.

2. The method according to claim 1, wherein an endogenous V-gene segment or a fragment thereof in said endogenous V-gene immunoglobulin locus of said chicken immunoglobulin expressing B lymphoid cell is replaced with said transgenic target nucleic acid sequence.

3. The method according to claim 1, wherein said chicken immunoglobulin expressing B lymphoid cell is capable of homologous recombination and DNA repair.

4. The method according to claim 1, wherein said chicken immunoglobulin expressing B lymphoid cell is a chicken Bursal lymphoma cell.

5. The method according to claim 1, wherein said chicken immunoglobulin expressing B lymphoid cell is a DT40 cell or a derivative thereof.

6. The method according to claim 1, wherein said target nucleic acid sequence encodes a protein or possesses a regulatory activity.

7. The method according to claim 1, wherein said target nucleic acid sequence encodes a protein selected from the group consisting of an immunoglobulin chain, a selection marker, a DNA-binding protein, a DNA-binding protein fragment, an enzyme, a receptor protein, and a receptor protein fragment.

8. The method according to claim 1, wherein said target nucleic acid sequence is a human immunoglobulin V-gene segment or a part thereof.

9. The method according to claim 1, wherein said target nucleic acid sequence comprises a transcription regulatory element or an interfering RNA (RNAi) sequence.

10. The method according to claim 9, wherein said transcription regulatory element is a promoter.

11. The method according to claim 1, further comprising (d) identifying said chicken immunoglobulin expressing B lymphoid cell containing said hypermutated transgenic target nucleic acid sequence.

12. The method according to claim 11, wherein said identifying said chicken immunoglobulin expressing B lymphoid cell containing said hypermutated transgenic target nucleic acid sequence comprises identifying a protein encoded by said hypermutated transgenic target nucleic acid sequence on the surface of said chicken immunoglobulin expressing B lymphoid cell, within said chicken immunoglobulin expressing B lymphoid cell, or outside of said chicken immunoglobulin expressing B-lymphoid cell.

13. The method according to claim 1, further comprising modulating hypermutation of said target nucleic acid sequence with a DNA repair or recombination factor other than a XRCC2, XRCC3, and RAD51 protein or their analogue.

14. The method according to claim 13, wherein said DNA repair or recombination factor is a RAD54 protein.

15. The method according to claim 1, wherein said chicken immunoglobulin expressing B lymphoid cell has no pseudo-V gene segment.

16. The method according to claim 1, wherein hypermutation is at a rate above an order of $10^{-9}$ to $10^{-10}$ $bp^{-1}$ generation$^{-1}$.

17. The method according to claim 1, wherein hypermutation is at a rate between $10^{-5}$ to $10^{-3}$ $bp^{-1}$ generation$^{-1}$.

18. The method according to claim 11, wherein a gene product of said hypermutated transgenic target nucleic acid sequence has an optimized desired activity.

19. The method according to claim 11, wherein said identifying further comprises (e) culturing said chicken immunoglobulin expressing B lymphoid cell under appropriate conditions to express a mutated gene product encoded by said hypermutated transgenic target nucleic acid sequence; (f) identifying said cultured chicken immunoglobulin expressing B lymphoid cell that expresses said mutated gene product having a desired activity; (g) establishing a clonal population of cells from said cultured chicken immunoglobulin expressing B lymphoid cell; and (h) selecting from said clonal population a cell that expresses a gene product of said hypermutated transgenic target nucleic acid sequence having an improved desired activity.

20. The method according to claim 19, wherein steps (f) through (h) are iteratively repeated.

21. The method according to claim 19, further comprising inhibition of hypermutation.

22. The method according to claim 21, wherein said inhibition of hypermutation is by down-regulation of the expression of a trans-acting regulatory factor.

23. The method according to claim 22, wherein said trans-acting regulatory factor is activation-induced deaminase (AID).

24. The method according to claim 5, wherein said chicken immunoglobulin expressing B lymphoid cell has no pseudo-V gene segment.

25. The method according to claim 1, wherein said chicken immunoglobulin expressing B lymphoid cell is a DT40 $AID^R\Psi V^-$ cell.

* * * * *

UNITED STATES PATENT AND TRADEMARK OFFICE
CERTIFICATE OF CORRECTION

PATENT NO. : 8,518,699 B2  
APPLICATION NO. : 10/590211  
DATED : August 27, 2013  
INVENTOR(S) : Buerstedde et al.

Page 1 of 2

It is certified that error appears in the above-identified patent and that said Letters Patent is hereby corrected as shown below:

In the Specifications

Col. 12 Line 22-23, insert Table 1 as shown on attached page.

Signed and Sealed this
Eleventh Day of March, 2014

Michelle K. Lee
*Deputy Director of the United States Patent and Trademark Office*

Table 1 Mutation profile

| Cell line | Gene | Mutation Ratio | | | Mutated sequences /total | Type of mutation | | | |
|---|---|---|---|---|---|---|---|---|---|
| | | Mutation events | Total bp sequenced | Frequency: mutation/bp $(\times 10^{-3})$ | | Point mutation (non-templated) | Gene conversion | Deletion | Insertion |
| AID$^R$ψV$^-$ | VJ | 135 | 45220 | 2,99 | 70/95 (73,7%) | 133 | - | 2 | 0 |
| | Bu-1 | 1 | 47500 | 0,02 | 1/95 (1,1%) | 0 | - | 1 | 0 |
| | EFIα | 2 | 42720 | 0,05 | 2/89 (2,2%) | 2 | - | 0 | 0 |
| | VJC (cDNA) from sorted IgM (-) | 245 | 80276 | 3,05 | 87/94 (92,6%) | 239 | - | 5 | 1 |
| AID$^{-/-}$ψV$^-$ | VJ | 0 | 45220 | 0,00 | 0/95 (0.0%) | 0 | - | 0 | 0 |
| AID$^R$ψV$^{par}$ | VJ | 110 | 46354 | 2,37 | 65/98 (66,3%) | 87(80) | 18 | 4 | 1 |
| AID$^{-/-}$ψV$^{par}$ | VJ | 3 | 43516 | 0,07 | 3/92(3,3%) | 3 | 0 | 0 | 0 |
| AID$^R$ | VJ | 112 | 25960 | 4,31 | 55/55 (100,0%) | 39(9) | 72 | 1 | 0 |
| AID$^{-/-}$ | VJ | 3 | 39732 | 0,08 | 3/84 (3,6%) | 3 | 0 | 0 | 0 |
| XRCC3$^{-/-}$ | VJ | 56 | 44462 | 1,26 | 38/94 (40,4%) | 55(40) | 1 | 0 | 0 |

SEQUENCE LISTING

<160> NUMBER OF SEQ ID NOS: 16

<210> SEQ ID NO 1
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: see specification as filed for detailed
      description of substitutions and preferred embodiments

<400> SEQUENCE: 1
tccctggtgc aggcagcgct gactcagccg gcctcggtgt cagcaaaccc aggagaaacc      60
gtcaagatca cctgctccgg gggtggcagc tatgctggaa gttactatta tggctggtac     120

-continued

```
cagcagaagt ctcctggcag tgcccctgtc actgtgatct atgacaacga caagagaccc      180
tcggacatcc cttcacgatt ctccggttcc aaatccggct ccacagccac attaaccatc      240
actggggtcc gagccgatga cgaggctgtc tatttctgtg ggagctacga agacaacagt      300
ggtgctgcat ttggggccgg acaaccctg accgtcctag gtgagtcgct gacctcgtct       360
cggtctttct tcccccatcg tgaaattgtg acattttgtc gattttggt gatttggggg       420 tttttcttgg acttggcggc aggctggggt ctgccaccgg cgcagggccg ggcact          476
```

<210> SEQ ID NO 2
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: see specification as filed for detailed
      description of substitutions and preferred embodiments

<400> SEQUENCE: 2

```
tccctggtgc aggcagcgct gactcagccg gcctcggtgt cagcaaaccc aggagaaacc       60
gtcaagatca cctgctccgg gggtggcagc tatgttggaa gttactatta tggctggtac      120
cagcagaagt ctcctggcag tgcccctgtc actgtgatct atgacaacga caagagaccc      180
tcggacatcc cttcacgatt ctccggttcc aaatccggct ccacagccac attaaccatc      240
actggggtcc gagccgatga cgaggctgtc tatttctgtg ggagcactgc agacaacagt      300
ggtgctgcat ttggggccgg acaaccctg accgtcctag gtgagtcgct gacctcgtct       360
cggtctttct tcccccatcg tgaaattgtg acattttgtc gattttggt gatttggggg       420 tttttcttgg acttggcggc aggctggggt ctgccaccgg cgcagggccg ggcact          476
```

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
ggtagcggct at                                                           12
```

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
aacctgggag gaaccgtcga gatcacctgc tccgggggtt acagcggcta tgcctgga        58
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
tggaagttac tattatggct ggtacc                                            26
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tataatggca ataacaga                                                 18

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atctactatg atgatgagag accctcgaac atc                                33

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggttctggat ccggctccac aaacaca                                       27

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggtacgaag ac                                                       12

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctatctatt actgt                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gggagctgca tagac                                                    15

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tattactgtg ggtgcataga c                                               21

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gggaagcttg atcatttcct gaatgctata ttca                                 34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggtctagaa actcctaggg gaaactttgc tgag                                 34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggaagcttc ggaagaaaga agctaaagac catc                                 34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggggctagca aagagcgtg ctcacgggtc tgcc                                  34
```